United States Patent
Picha et al.

(10) Patent No.: US 9,133,833 B2
(45) Date of Patent: Sep. 15, 2015

(54) METHODS AND APPARATUS FOR MOVING ALIQUOT SAMPLES OF FLUID

(75) Inventors: Neil Picha, Petaluma, KS (US); Bruce Black, Napa, CA (US); Kristine Olsen, Wausaukee, WI (US); James Anderson, Jr., Arlington Heights, IL (US); Washington Mendoza, Lake in the Hills, IL (US); Raaidah Saari-Nordhaus, Antioch, IL (US); Josef Bystron, Chicago, IL (US)

(73) Assignee: Alltech Associates, Inc., Columbia, MD (US)

(*) Notice: Subject to any disclaimer, the term of this patent is extended or adjusted under 35 U.S.C. 154(b) by 727 days.

(21) Appl. No.: 13/132,619

(22) PCT Filed: Dec. 4, 2009

(86) PCT No.: PCT/US2009/006397
§ 371 (c)(1),
(2), (4) Date: Dec. 12, 2011

(87) PCT Pub. No.: WO2010/065138
PCT Pub. Date: Jun. 10, 2010

(65) Prior Publication Data
US 2012/0073665 A1    Mar. 29, 2012

Related U.S. Application Data

(60) Provisional application No. 61/200,814, filed on Dec. 4, 2008.

(51) Int. Cl.
*F15D 1/00* (2006.01)
*F04B 19/00* (2006.01)
(Continued)

(52) U.S. Cl.
CPC .......... *F04B 19/006* (2013.01); *G01N 35/1097* (2013.01); *G01N 2030/204* (2013.01); *Y10T 137/0318* (2015.04); *Y10T 137/8593* (2015.04)

(58) Field of Classification Search
CPC .................. Y10T 137/8593; Y10T 137/0318; G01N 2030/204; F15D 1/00
USPC .......... 73/61.55, 61.56, 61.59, 64.56, 863.31, 73/863.71, 863.73, 863.83; 137/595, 597, 137/625.19, 625.46; 222/71, 420; 285/124.1, 124.2
See application file for complete search history.

(56) References Cited

U.S. PATENT DOCUMENTS

| | | | |
|---|---|---|---|
| 3,146,793 A | 9/1964 | Fay et al. | 137/625.11 |
| 3,758,235 A | 9/1973 | Breeden | 417/222 |

(Continued)

FOREIGN PATENT DOCUMENTS

| | | | | |
|---|---|---|---|---|
| EP | 1380329 | 1/2004 | | B01D 15/08 |
| EP | 1370571 | 6/2005 | | C07K 1/36 |

(Continued)

OTHER PUBLICATIONS

Automated Semipreparative Purification with Mass Spectrometric Fraction Collection Trigger: Modeling and Experimental Evaluation Evaluation of a Setup Employing Passive Splitting by Steiner, F., Mahsunah A., Arnold F., Piecha T., Huber C.; J. Sep. Sci 2007, 30, 1496-1508.

(Continued)

*Primary Examiner* — Peter Macchiarolo
*Assistant Examiner* — Alexander Mercado
(74) *Attorney, Agent, or Firm* — Beverly J. Artale

(57) ABSTRACT

Methods and apparatus for moving aliquot samples of fluid using a shuttle valve are disclosed.

17 Claims, 8 Drawing Sheets

(51) Int. Cl.
G01N 35/10 (2006.01)
G01N 30/20 (2006.01)

(56) References Cited

U.S. PATENT DOCUMENTS

| | | | | |
|---|---|---|---|---|
| 3,948,104 | A | 4/1976 | Stephens | 73/422 |
| 4,059,009 | A | 11/1977 | Ball et al. | 73/61.1 |
| 4,066,411 | A | 1/1978 | Fine et al. | 23/253 |
| 4,158,630 | A | 6/1979 | Stearns | 210/198 |
| 4,357,420 | A | 11/1982 | Bostick et al. | 435/8 |
| 4,494,677 | A * | 1/1985 | Falcoff | 222/63 |
| 4,506,558 | A | 3/1985 | Bakalyar | 73/863.72 |
| 4,726,932 | A * | 2/1988 | Feier et al. | 422/501 |
| 4,957,008 | A * | 9/1990 | Proni et al. | 73/864.83 |
| 5,010,921 | A | 4/1991 | Nohl | 137/625.46 |
| 5,149,658 | A * | 9/1992 | Cassaday et al. | 436/53 |
| 5,227,135 | A | 7/1993 | Godec et al. | 422/98 |
| 5,234,586 | A | 8/1993 | Afeyan et al. | 210/198.2 |
| 5,306,426 | A | 4/1994 | Afeyan | 210/635 |
| 5,495,108 | A | 2/1996 | Apffel et al. | 250/288 |
| 5,542,305 | A * | 8/1996 | Hollinger | 73/863.73 |
| 5,803,117 | A * | 9/1998 | Olsen et al. | 137/625.15 |
| 6,012,488 | A * | 1/2000 | Nichols | 137/625.11 |
| 6,106,710 | A | 8/2000 | Fischer et al. | 210/198.2 |
| RE36,892 | E | 10/2000 | Apffel, Jr. et al. | 250/288 |
| 6,183,635 | B1 | 2/2001 | Klee et al. | 210/198.2 |
| 6,289,914 | B1 | 9/2001 | Tommasi | 137/15.18 |
| 6,294,087 | B1 | 9/2001 | Hargro et al. | 210/198.2 |
| 6,360,619 | B1 | 3/2002 | Schultz | 73/863.86 |
| 6,382,035 | B1 | 5/2002 | Nichols | 73/863.72 |
| 6,406,633 | B1 | 6/2002 | Fischer et al. | 210/659 |
| 6,436,292 | B1 | 8/2002 | Petro | 210/656 |
| 6,453,946 | B2 | 9/2002 | Nichols et al. | 137/625.15 |
| 6,461,515 | B1 | 10/2002 | Safir et al. | 210/656 |
| 6,627,075 | B1 | 9/2003 | Weissgerber et al. | 210/198.2 |
| 6,632,404 | B1 * | 10/2003 | Freitag et al. | 506/33 |
| 6,672,336 | B2 | 1/2004 | Nichols | 137/625.46 |
| 6,712,085 | B2 | 3/2004 | Weissgerber et al. | 137/12 |
| 6,730,228 | B2 | 5/2004 | Petro et al. | 210/656 |
| 6,767,467 | B2 | 7/2004 | Fischer et al. | 210/659 |
| 6,776,902 | B2 | 8/2004 | Petro | 210/198.2 |
| 6,855,258 | B2 | 2/2005 | Petro et al. | 210/656 |
| 6,890,489 | B2 | 5/2005 | Nichols et al. | 422/103 |
| 6,989,129 | B2 | 1/2006 | Licklider et al. | 422/70 |
| 7,169,308 | B2 | 1/2007 | Ohkura | 210/656 |
| 7,214,320 | B1 | 5/2007 | Gregori et al. | 210/656 |
| 7,267,796 | B2 | 9/2007 | Waki | 422/70 |
| 7,318,900 | B2 | 1/2008 | DeMarco | 210/656 |
| 7,322,808 | B2 | 1/2008 | Daigre | 418/61.3 |
| 7,419,598 | B2 | 9/2008 | Davison | 201/694 |
| 7,575,723 | B2 | 8/2009 | Nichols et al. | 422/103 |
| 7,686,959 | B2 | 3/2010 | Horsman et al. | 210/656 |
| 7,823,468 | B2 * | 11/2010 | Davison | 73/863.73 |
| 7,901,628 | B2 | 3/2011 | Yamamoto | 422/70 |
| 8,048,386 | B2 * | 11/2011 | Dority et al. | 422/500 |
| 8,277,434 | B2 * | 10/2012 | Haueter et al. | 604/500 |
| 8,431,413 | B2 * | 4/2013 | Dority et al. | 436/500 |
| 8,544,350 | B2 * | 10/2013 | Itafuji et al. | 73/864.83 |
| 2001/0013494 | A1 | 8/2001 | Maiefski et al. | 210/656 |
| 2001/0028071 | A1 | 10/2001 | Yoo et al. | 250/288 |
| 2001/0035516 | A1 * | 11/2001 | Nichols et al. | 251/368 |
| 2001/0038071 | A1 * | 11/2001 | Nichols et al. | 250/288 |
| 2002/0121468 | A1 | 9/2002 | Fischer et al. | 210/198.2 |
| 2002/0146349 | A1 | 10/2002 | Gygi et al. | 422/70 |
| 2002/0190001 | A1 | 12/2002 | Petro | 210/656 |
| 2003/0080062 | A1 | 5/2003 | Petro et al. | 210/656 |
| 2003/0089663 | A1 | 5/2003 | Petro et al. | 210/656 |
| 2003/0217608 | A1 * | 11/2003 | Brinker et al. | 73/864.34 |
| 2003/0224390 | A1 | 12/2003 | Fowlkes et al. | 435/6 |
| 2005/0118075 | A1 * | 6/2005 | Nichols et al. | 422/103 |
| 2005/0226778 | A1 | 10/2005 | Houser et al. | 422/99 |
| 2005/0239152 | A1 | 10/2005 | Irth et al. | 435/8 |
| 2006/0075806 | A1 | 4/2006 | Gilby et al. | 73/61.57 |
| 2006/0085139 | A1 | 4/2006 | Collette et al. | 702/20 |
| 2006/0093521 | A1 | 5/2006 | Swartz et al. | 422/70 |
| 2006/0192108 | A1 | 8/2006 | Yeatman et al. | 250/288 |
| 2006/0194335 | A1 * | 8/2006 | Berndtsson | 436/177 |
| 2006/0219637 | A1 | 10/2006 | Killeen et al. | 210/656 |
| 2006/0285108 | A1 | 12/2006 | Morrisroe | 356/316 |
| 2007/0023037 | A1 | 2/2007 | Larsen et al. | 128/200.18 |
| 2007/0056357 | A1 | 3/2007 | Ruegenberg et al. | 73/53.01 |
| 2007/0122314 | A1 | 5/2007 | Strand et al. | 422/100 |
| 2007/0132229 | A1 | 6/2007 | Mueller et al. | 285/124.2 |
| 2007/0181505 | A1 | 8/2007 | DeMarco et al. | 210/656 |
| 2009/0320925 | A1 * | 12/2009 | Nichols | 137/1 |
| 2010/0238444 | A1 | 9/2010 | Anderson et al. | 356/436 |
| 2011/0017670 | A1 | 1/2011 | Anderson et al. | 210/656 |
| 2011/0301865 | A1 * | 12/2011 | Anderson et al. | 702/24 |
| 2011/0301868 | A1 * | 12/2011 | Anderson et al. | 702/31 |
| 2011/0302994 | A1 * | 12/2011 | Anderson et al. | 73/23.35 |
| 2011/0310390 | A1 * | 12/2011 | Anderson et al. | 356/436 |
| 2012/0079874 | A1 * | 4/2012 | Anderson et al. | 73/61.53 |
| 2012/0096932 | A1 * | 4/2012 | Anderson et al. | 73/61.53 |
| 2012/0103073 | A1 * | 5/2012 | Bystron et al. | 73/61.53 |
| 2012/0166098 | A1 * | 6/2012 | McCreary et al. | 702/25 |
| 2012/0175289 | A1 * | 7/2012 | Bystron et al. | 210/91 |
| 2013/0042673 | A1 * | 2/2013 | Saari-Nordhaus et al. | 73/61.55 |

FOREIGN PATENT DOCUMENTS

| | | | |
|---|---|---|---|
| EP | 01707957 | 10/2006 | G01N 30/20 |
| EP | 1348958 | 9/2008 | G01N 30/60 |
| WO | 9925451 | 5/1999 | B01D 15/08 |
| WO | 9925452 | 5/1999 | B01D 15/08 |
| WO | 0026662 | 5/2000 | G01N 30/22 |
| WO | 0037157 | 6/2000 | B01D 15/08 |
| WO | 0045929 | 8/2000 | B01D 15/08 |
| WO | 0136071 | 5/2001 | B01D 57/02 |
| WO | 02063291 | 8/2002 | G01N 30/00 |
| WO | 02082071 | 10/2002 | G01N 30/08 |
| WO | 03008101 | 1/2003 | B01L 3/00 |
| WO | 03021251 | 3/2003 | G01N 30/88 |
| WO | 2005116628 | 12/2005 | G01N 30/80 |
| WO | 2006042365 | 4/2006 | G01N 30/89 |
| WO | WO 2008070776 A2 * | 6/2008 | G01N 30/84 |
| WO | 2008118808 | 10/2008 | G01N 30/80 |

OTHER PUBLICATIONS

Blue Natural Organic Dyestuffs—From Textile Dyeing to Mural Painting. Seperation and Characterization of Coloring Matters Presents in Elderberry, Logwood and Indigo by Pawlak, J., Puchalska, M., Miszczak, A., Rostoniec, E., and Jarosz, M.,; Journal of Mass Spectrometry 2006; 41: 613-622.

High-Throughput Purification of Combinatorial Libraries I: A High-Throughput Purification System Using and Accelerated Retention Window Approach by Yan, B., Collins, N., Wheatley, J., Irving, M., Leopold, K., Chan, C., Shornikov, A., Fang, L., Lee, A., Stock, M., and Zhao, J.; J. Comb Chem. 2004, 6, 255-261.

Optimal Fraction Collecting in Preparative LC/MS by Rosentreter, T. and Huber, U.; Journal of Combinatorial Chemistry, vol. 6, No. 2.

Purification of Alkaloids from *Corydalis yanhusuo* W.T. Wang Using Preparative 2-D HPLC by Zhang, Jing; Jin, Yu; Liu, Yanfang; Xiao, Yuansheng; Feng, Jiateo; Xue, Xingya; Zhang, Xiull; Liang, Xinmaio; J. Sep. Sci. 2009, 31, 1401-1406.

Quantification of fipronil and its metabolite fipronil sulfone in rat plasma over a wide range of concentrations by LC/UV/MS by Lacroix, M Z; Puel, S; Toutain, P L; Viguioe, C.; J Chromatogr B Analyt Technol Biomed Life Sci vol. 878, No. 22.

Role of mass spectrometry in the purification of peptides and proteins by Mazza, C. B.; Cavanaugh, J. Y.; Neue, U. D.; Phillips, D. J.; J. Chromatogr. B Anal. Technol. Biomed. Life Sci vol. 790.

Sample preparation for hyphenated analytical techniques by Rosenfeld, J.M.; p. 121-123.

Separation and Identification of Compounds in *Adinandra* Nitida by Comprehensive Two-Dimensional Liquid Chromatography Coupled to Atmospheric Pressure Chemical Ionization Source Ion Trap Tandem Mass Spectrometry by J. Zhang, D. Tao, J. Duan, Z. Liang, W. Zhang, L. Zhang, Y. Huo, and Y. Zhang. From Anal Bioanal Chem (2006) 386: 586-593.

(56) References Cited

OTHER PUBLICATIONS

On-Line Sample Enrichment System Coupled to Electrospray Ionization Time-of-Flight Mass Spectrometry (ESI-TOF-MS) by M. Okamoto, K. Yamashita, and K. Nakai from Journal of Pharmaceutical and Biomedical Analysis 41 (2006) 707-713.

Liquid Chromatography with Ultraviolet Absorbance-Mass Spectrometric Detection and with Nuclear Magnetic Resonance Spectroscopy: A Powerful Combination for the On-Line Structural investigation of Plant Metabolites by J. Wolfender, K Ndjoko, and K Hostettmann from Journal of Chromatography A, 1000 (2003) 437-455.

A Straightforward Means of Coupling Preparative High-Perfromance Liquid Chromatography and Mass Spectrometry by H. Cai, J. Kiplinger, W. Goetzinger, R. Cole, K. Laws, M. Foster, and A Schrock from Rapid Communications in Mass Spectrometry (2002) 16: 544-554.

A novel hyphenated LC-ARC-RD-MS-FC system for identification of drug metabolites; Proceedings of the 50th ASMS Conference on Mass Spectrometry and Allied Topics, Orlando Florida, Jun. 2-6, 2002 by Wenzhe Lu, ChungPing Yu, Dian Y. Lee.

Analysis of Rhubarb by Liquid Chromatography-Electrospray-Mass Spectrometry; Tamkang Journal of Science and Engineering, Vlk. 6, No. 1, pp. 31-36 (2003) by Ming-Ren S. Fuh and Hung-Jian Lin.

Automated simultaneous isolation and quantitation of labeled amino acid fractions from plasma and tissue by ion-exchange chromatography; Journal of Chromatography B, 660 (1994) 251-257 by Hans M.H. van Eijik, Mark P.L. Huinck, Dennis R. Rooyakkers, Nicolaas E.P. Deutz.

Characterization of apolipoprotein and apollpoprotein precursors in pancreatic cancer serum samples via two-dimensional liquid chromatography and mass spectrometry; Journal of Chromatography A. 1162 (2007) 117-125 by Jianzhong Chen, Michelle Anderson, David E. Misek, Diane M. Simeone, and David M Libman.

Evaluation of applicability of the flow splitter to frit-FAB LC-MS system; Mass Spectroscopy vol. 39, No. 4, Aug. 1991 by Yoshitomo Ikai, Hisao Oka, Junko Hayakawa, Ken-ichi Harada, and Makato Suzuki.

High-Throughput Mass-Directed Parallel Purification Incorporating a Multiplexed Single Quadrupole Mass Spectrometer; Anal. Chem. 2002, 74, 3055-3062 by Rongda Xu, Tao Wang, John Isbell, Zhe Cai, Christopher Sykes, Andrew Brallsford, and Daniel B. Kassel.

Hyphenation of centrifugal partition chromatography with electrospray ionization mass spectrometry using an active flow-splitter device for characterization of flavonol glycosides; Rapid Communications in Mass Spectrometry 2009; 23; 1863-1870 by Alix Toribio, Emilie Desandau, Claire Elfakir, and Michel Lafosse.

Hyphenation of high performance liquid chromatography with sector field inductively coupled plasma mass spectrometry for the determination of ultra-trace level anionic and cationic arsenic compounds in freshwater fish; J. Anal. At. Spectrom., 2004, 19, 191-195 by Jian Zheng and Holger Hintelmann.

Identification of intact glucosinolates using direct coupling of high-performance liquid chromatography with continuous-flow frit fast atom bombardment tandem mass spectrometry; Biological Mass Spectrometry, vol. 20, 259-263 (1991) by P.S. Kokkonen, J. van der Greef, W.M.A. Niessen, U.R. Tjaden, G.J. ten Hove, and G. van de Werken.

Improved liquid chromatography—mass spectrometry performance in quantitative analysis using a nanosplitter interface; Journal of Chromatography A. 1053 (2004) 151-159 by Christine L. Andrews, Chung-Ping Yu, Eric Yang, and Paul Vouros.

Novel system for separation of phospholipids by high-performance liquid chromatography; Journal of Chromatography, 234 (1982) 218-221 by Iftekhar Alam, J. Bryan Smith, Melvin J. Silver, and David Ahern.

Optimization of a liquid chromatography method based on simultaneous electrospray ionization mass spectrometric and ultraviolet photodiode array detection for analysis of flavonoid glycosides; Rapid Communications in Mass Spectrometry 2002; 16: 2341-2348 by Filip Cuyckens and Magda Claeys.

Quantitation of Radiolabeled Compounds Eluting from the HPLC System; Journal of Chromatographic Science, vol. 20, Nov. 1982 by Michael J. Kessler.

Rapid Analysis of antiobiotic-containing mixtures from fermentation broths by using liquid chromatography-electrospray ionization-mass spectrometry and matrix-assisted laser desorption ionization-time-of-flight-mass spectrometry; American Society for Mass Spectrometry, 1996, 7, 1227-1237 by Bradley L. Ackermann, Brian T. Regg, Luigi Colombo, Sergio Stella, and John E. Coutant.

On-Line Mass Characterization of Fractions in a Muiti-Channel Preparitive HPLC Environment by Liu J., Bickler, J., Rahn, P.C., R & D Biotage., Inc.; Abstracts of Papers American Chemical Society, vol. 223 (2002).

* cited by examiner

METHODS AND APPARATUS FOR MOVING ALIQUOT SAMPLES OF FLUID

CROSS REFERENCE TO RELATED APPLICATION

This application claims the benefit of U.S. patent application Ser. No. 61/200,814, filed Dec. 4. 2008.

FIELD OF THE INVENTION

The present invention is directed to methods and apparatus for moving aliquot samples of fluid.

BACKGROUND OF THE INVENTION

There is a need in the art for methods of efficiently and effectively moving aliquot samples of fluid. There is also a need in the art for an apparatus capable of effectively moving aliquot samples of fluid.

SUMMARY OF THE INVENTION

The present invention relates to the discovery of methods for moving aliquot samples of fluid. The disclosed methods provide a number of advantages over known methods of moving aliquot samples of fluid. For example, the disclosed methods of the present invention may be utilized to remove a very small sample volume, or aliquot, of fluid from a much larger volume of fluid, such as the flow of a stream through a channel. The disclosed methods of the present invention may also be utilized to remove a very small sample volume, or aliquot, of fluid from a much larger volume of fluid, such as the flow of a stream through a channel, and transfer the sample to another volume of fluid or container.

The present invention is directed to methods of moving aliquot samples of fluid. In one exemplary embodiment, the method of moving an aliquot sample of fluid comprises the steps of providing a first fluid, providing a second fluid, using a shuttle valve to remove an aliquot from the first fluid to the second fluid while maintaining a continuous flow path through the shuttle valve of the second fluid. In one embodiment, the first fluid comprises a continuous flow path through the shuttle valve which remains open when the aliquot is removed from the first fluid. In another embodiment, both the first fluid and the second fluid comprise continuous paths through the shuttle valve which remain open as the aliquot sample is removed from the first fluid.

In another exemplary embodiment according to the present invention, a method of moving an aliquot sample of fluid includes the steps of providing a first fluid; using a shuttle valve to remove an aliquot sample from the first fluid without substantially affecting flow properties of the first fluid through the shuttle valve. At least a portion of flow of the first fluid through the shuttle valve may be substantially laminar, due to at least a portion of the first fluid flow path being substantially straight through the valve. In a further exemplary embodiment, the pressure of the first fluid through the shuttle valve remains substantially constant and/or it does not substantially increase. In an alternative embodiment, the aliquot sample is transferred from a first fluid to a second fluid. The second fluid may comprise a continuous flow path through the shuttle valve.

In a further exemplary embodiment according to the present invention, the method of moving an aliquot sample of fluid comprises the steps of providing a static body having at least two channels therethrough such that at least a portion of each channel is parallel to and intersects with a first surface of the static body, providing a dynamic body having an aliquot dimple that intersects with a first surface of the dynamic body, the first surface of the static body and dynamic body being contiguous with each other and the channels and the aliquot dimple located such that the aliquot dimple may be in fluid communication with one channel in a first position and in fluid communication with another channel in a second position, flowing a first fluid through one of said channels, flowing a second fluid through another of said channels, aligning the aliquot dimple in the first position, allowing a sample portion of the first fluid to flow into the aliquot dimple, and moving the aliquot dimple to the second position, whereby the sample portion is transferred to the second fluid.

The present invention is also directed to an apparatus capable of moving an aliquot sample of fluid. In one exemplary embodiment, the apparatus for moving an aliquot sample of fluid comprises hardware operatively adapted to remove a very small sample volume, or aliquot, of fluid from a much larger volume of fluid, for example, such as the flow of a stream through a channel. The disclosed apparatus of the present invention may also be utilized to remove a very small sample volume, or aliquot, of fluid from a much larger volume of fluid, for example, such as the flow of a stream through a channel, and transfer the sample to another volume of fluid or container.

In one exemplary embodiment, an apparatus capable of moving an aliquot sample of fluid comprises a first fluid, a second fluid, and a shuttle valve capable of removing an aliquot from the first fluid to the second fluid while maintaining a continuous flow path through the shuttle valve of the second fluid. In one embodiment, the apparatus is capable of removing the aliquot from the first fluid while maintaining a continuous flow path through the shuttle valve of the first fluid. In another embodiment, the apparatus is capable of removing the aliquot from the first fluid while maintaining continuous flow paths of both the first fluid and the second fluid.

In another embodiment according to the present invention, an apparatus capable of moving an aliquot sample of fluid comprises a first fluid channel, a second fluid channel, and a shuttle valve capable of removing an aliquot of fluid from the first channel to the second channel without substantially affecting the flow properties of fluid in the first channel through the valve. At least a portion of the first channel through the valve may be substantially straight. In this embodiment, the pressure of fluid in the first channel through the shuttle valve does not substantially increase. In another exemplary embodiment, at least a portion of the first channel may be substantially parallel to the aliquot dimple, which provides laminar flow of fluid in the first channel through the valve. In a further embodiment, at least a portion of the second channel through the valve may be substantially straight. In this embodiment, the pressure of fluid in the second channel through the shuttle valve does not substantially increase. In another exemplary embodiment, the second channel may be substantially parallel to the aliquot dimple, which provides laminar flow of fluid in the second channel through the valve.

In a further exemplary embodiment according to the present invention, an apparatus capable of moving an aliquot sample of fluid comprises a static body having at least two channels therethrough such that a portion of each channel intersects with a first surface of the static body, a dynamic body having an aliquot dimple that intersects with a first surface of the dynamic body, the first surface of the static body and the first surface of the dynamic body being contiguous with each other, and the channels and the aliquot dimple located such that the aliquot dimple may be in fluid communication with one channel in a first position and in fluid communication with another channel in a second position, wherein at least a portion of the first channel is substantially parallel to the first surface of the static body. In an alternative exemplary embodiment, at least a portion of the first channel through the valve may be substantially straight. In an exemplary embodiment, the pressure of fluid in the first channel through the shuttle valve does not substantially increase. In another exemplary embodiment, at least a portion of the first channel may be substantially parallel to the aliquot dimple. In an exemplary embodiment, the flow of fluid in the first channel through the valve is laminar. In a further embodiment, at least a portion of the second channel through the valve may be substantially straight. In a further embodiment, the pressure of fluid in the second channel through the shuttle valve does not substantially increase. In another exemplary embodiment, the second channel may be substantially parallel to the aliquot dimple. In an embodiment, the flow of fluid in the second channel through the valve may be laminar.

In a further exemplary embodiment according to the present invention, an apparatus capable of moving an aliquot sample of fluid comprises a static body having at least two channels therethrough such that a portion of each channel intersects with a first surface of the static body, a dynamic body having an aliquot dimple that intersects with a first surface of the dynamic body, the first surface of the static body and the first surface of the dynamic body being contiguous with each other, and the channels and the aliquot dimple located such that the aliquot dimple may be in fluid communication with one channel in a first position and in fluid communication with another channel in a second position, wherein at least a portion of the second channel is substantially parallel to the first surface of the static body.

In a further exemplary embodiment, the apparatus of the present invention may be configured such that the static body includes an aliquot dimple and the dynamic body includes at least two channels therethrough. Moreover, the apparatus of the present invention may include at least one body that is dynamic, such as for example, two or more dynamic bodies with no static body.

These and other features and advantages of the present invention will become apparent after a review of the following detailed description of the disclosed embodiments and the appended claims.

DETAILED DESCRIPTION OF THE INVENTION

Figure 1:
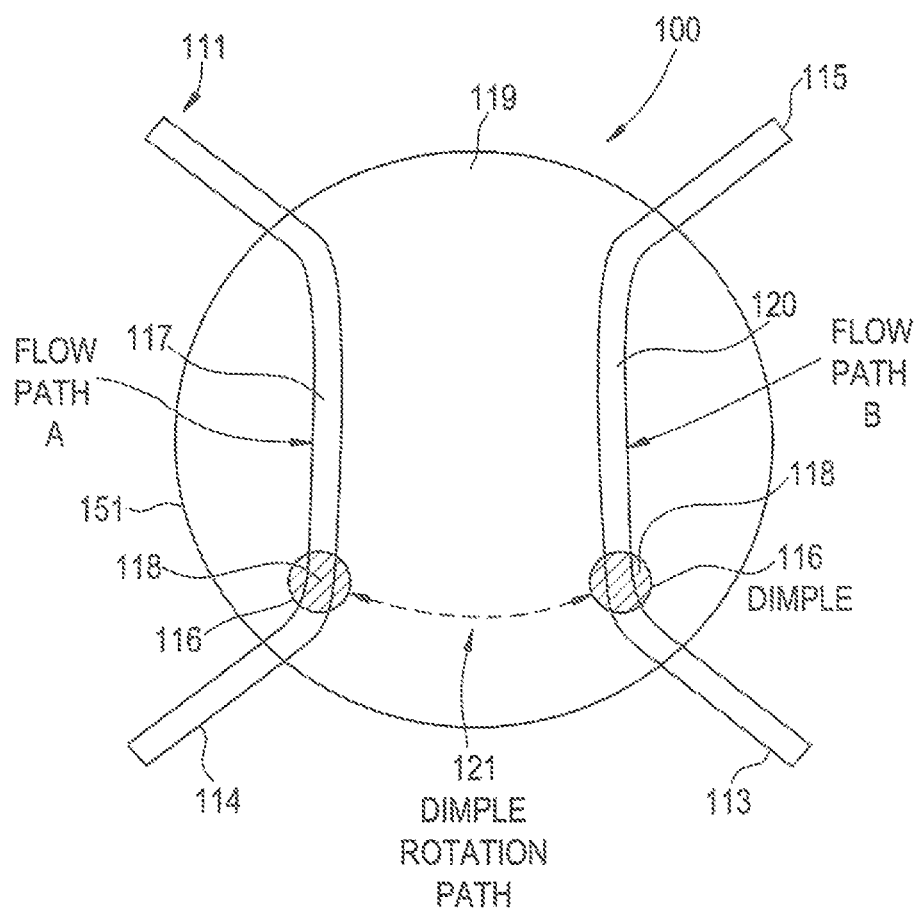
FIG. 1 depicts the operation of an exemplary shuttle valve suitable for use in the present invention.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "a solvent" includes a plurality of such solvents and reference to "solvent" includes reference to one or more solvents and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "shuttle valve" means a control valve that regulates the supply of fluid from one or more source(s) to another location. The shuttle valve may utilize rotary or linear motion to move a sample from on fluid to another and may be configured such that at least one body or part is dynamic.

As used herein, the term "fluid" means a gas, liquid, and supercritical fluid.

As used herein, the term "laminar flow" means smooth, orderly movement of a fluid, in which there is no turbulence, and any given subcurrent moves more or less in parallel with any other nearby subcurrent.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

The present invention is directed to methods of moving aliquot samples of fluid. The present invention is further directed to apparatus capable of moving aliquot samples of fluid. The present invention is even further directed to computer software suitable for use in an apparatus or apparatus component that is capable of moving aliquot samples of fluid, wherein the computer software enables the apparatus to perform one or more method steps as described herein.

A description of exemplary methods of moving aliquot samples of fluid and apparatus capable of moving aliquot samples of fluid is provided below.

I. Methods of Moving Aliquot Samples of Fluid

The present invention is directed to methods of moving aliquot samples of fluid. The methods of moving aliquot samples of fluid may contain a number of process steps, some of which are described below.

In this exemplary embodiment, the shuttle valve according to the present invention actively controls the transfer of aliquot sample of fluid from one vessel or stream to another. As used herein, the phrase "actively controls" refers to the ability of a given shuttle valve to control fluid transfer from one vessel or stream to another even though there may be changes in fluid flow rate of the streams through the shuttle valve. Unlike "passive" flow splitters that merely split fluid flow, the shuttle valves used in the present invention control removal of aliquot samples of fluid from one steam to the other regardless of possible fluctuations in fluid flow within the sample stream such as, for example, flow restrictions, total flow rate, temperature, and/or solvent composition.

The step of actively controlling transfer of aliquot samples of fluid from one stream or vessel to another may comprise, for example, sending an activation signal to a shuttle valve of the present invention to (i) activate the shuttle valve, (ii) deactivate the shuttle valve, (iii) change one or more flow and/or pressure settings of the shuttle valve, or (iv) any combination of (i) to (iii). Suitable flow and pressure settings include, but are not limited to, (i) a valve position, (ii) shuttle valve pressure, (iii) air pressure to a valve, or (iv) any combinations of (i) to (iii). Typically, the activation signal is in the form of, for example, an electrical signal, a pneumatic signal, a digital signal, or a wireless signal.

In one exemplary embodiment, the method of moving an aliquot sample of fluid comprises the steps of providing a first fluid, providing a second fluid, using a shuttle valve to remove an aliquot from the first fluid to the second fluid while maintaining a continuous flow path through the shuttle valve of the second fluid. In one embodiment, the first fluid comprises a continuous flow path through the shuttle valve which remains open when the aliquot is removed from the first fluid. In another embodiment, both the first fluid and the second fluid comprise continuous paths through the shuttle valve which remain open as the aliquot sample is removed from the first fluid.

In another exemplary embodiment according to the present invention, a method of moving an aliquot sample of fluid includes the steps of providing a first fluid; using a shuttle valve to remove an aliquot sample from the first fluid without substantially affecting flow properties of the first fluid through the shuttle valve. At least a portion of flow of the first fluid through the shuttle valve may be substantially laminar, due to at least a portion of the first fluid flow path being substantially straight through the valve. In a further exemplary embodiment, the pressure of the first fluid through the shuttle valve remains substantially constant and/or it does not substantially increase. In an alternative embodiment, the aliquot sample is transferred from a first fluid to a second fluid. The second fluid may comprise a continuous flow path through the shuttle valve.

In a further exemplary embodiment according to the present invention, the method of moving an aliquot sample of fluid comprises the steps of providing a static body having at least two channels therethrough such that at least a portion of each channel is parallel to and intersects with a first surface of the static body, providing a dynamic body having an aliquot dimple that intersects with a first surface of the dynamic body, the first surface of the static body and dynamic body being contiguous with each other and the channels and the aliquot dimple located such that the aliquot dimple may be in fluid communication with one channel in a first position and in fluid communication with another channel in a second position, flowing a first fluid through one of said channels, flowing a second fluid through another of said channels, aligning the aliquot dimple in the first position, allowing a sample portion of the first fluid to flow into the aliquot dimple, and moving the aliquot dimple to the second position, whereby the sample portion is transferred to the second fluid.

Figure 2:
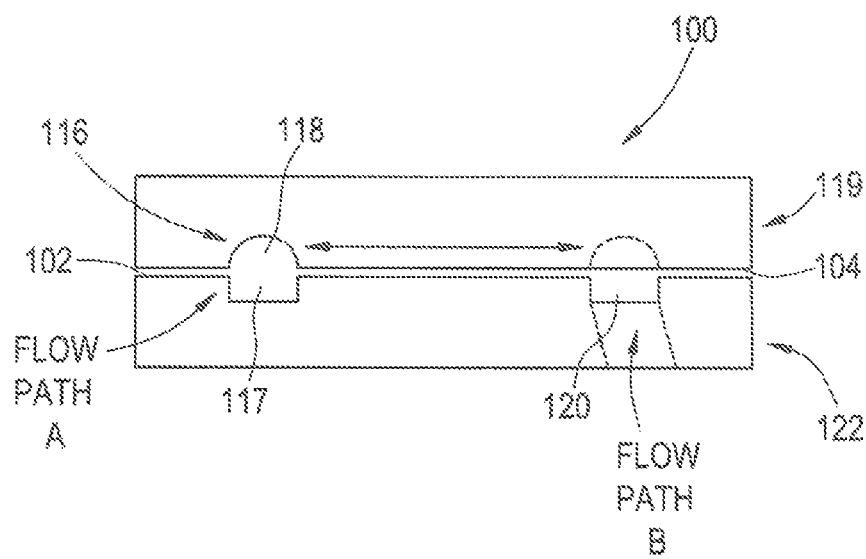
FIG. 2 depicts a cross-sectional view of an exemplary shuttle valve suitable for use in the present invention.

FIGS. 1-2 depict an exemplary shuttle valve of the present invention and how it operates by removal of an aliquot sample of fluid from one fluid stream to another. As shown in FIG. 1, shuttle valve 100 comprises an inlet 111 of a first stream, which provides fluid flow from a sample stream or vessel to shuttle valve 100; channel 117 connecting inlet 111 to an outlet 114 of the first stream; an incoming sample aliquot volume 118 in dimple 116 of dynamic body 119; outlet 114 provides fluid flow from shuttle valve 100 to the sample stream or vessel, or a different stream or vessel; inlet 115, which provides fluid flow of a second stream through shuttle valve 100; outgoing sample aliquot volume 118 in dimple 116; channel 120 connecting inlet 115 to outlet 113, which provides fluid flow through the shuttle valve 100 to a another stream or vessel.

As fluid flows through shuttle valve 100 from to inlet 111 to outlet 114 via channel 117, incoming sample aliquot volume 118 in dimple 116 is filled with a specific volume of fluid referred to herein as sample aliquot 118 (shown as the shaded area in FIG. 1). At a desired time, shuttle valve 100 transfers sample aliquot 118 within dimple 116 taken from channel 117 to channel 120 by rotating the dimple 116 in dynamic body 119 via dimple rotation path 121. Once sample aliquot 118 is transferred into channel 120, gas or liquid flowing from inlet 115 through channel 120 transports sample aliquot 118 to outlet 113. Another advantage of the shuttle valve of the present invention relates to the fluidics design of the channels through the valve. In order to minimize backpressure through the valve, the flow through channels 117 and 120 is continuous. This is accomplished by locating channels 117 and 120 in static body 122 such that no matter what position the dynamic body 119 is in, the flow through shuttle valve 100 is continuous (as shown in FIG. 2). As shown in FIG. 1, at least a portion of the channel 117 and channel 120 may be substantially planar and/or linear, which reduces turbulence and further minimizes pressure increase through the valve. In addition, at least a portion of the channel 117 and channel 120 may be substantially parallel to dimple 116, which further limits turbulent flow and any increase in pressure in the valve. For example, the term "substantially increase the pressure" through the shuttle valve would include those configurations that do not increase pressure within the valve of more than 50 psi, preferably not more than 30 psi, more preferably not more than 20 psi, and even more preferably not more than 10, 9, 8, 7, 6, 5, 4, 3, 2, or 1 psi. Dimple 116 is located in the dynamic body 119 and is in fluid communication with the face of the dynamic body that is contiguous with the static body 122, whereby when the dynamic body 119 is in a first position, the dimple 116 will be in fluid communication with channel 117, and when moved to a second position, the dimple 116 will be in fluid communication with channel 120. The dimple 116 may be of any shape but is depicted as a concave semi sphere, and it may be or any size. In an exemplary embodiment, the dimple may be extremely small in size (e.g., less than 2000 preferably less than about 500 nL, more preferably less than about 100 nL, and even more preferably less than about 1 nL, but may include any size from 1 nL to 2000 nL, which allows for rapid sampling. In addition, small dimple 116 size allows for a very short dimple rotation path 121, which significantly reduces wear on the surfaces of the dynamic body 119 and the static body 122 and results in a shuttle valve 100 having extended service life before maintenance is required (e.g., more than 10 million cycles are possible before service).

Shuttle valve 100 may be programmed to remove a sample aliquot (e.g., sample aliquot 118) from a sample for transport to at least one detector at a desired sampling frequency. In one exemplary embodiment, the sampling frequency is at least 1 sample aliquot every 10 seconds (or at least 1 sample aliquot every 5 seconds, or at least 1 sample aliquot every 3 seconds, or at least 1 sample aliquot every 2 seconds, or 1 sample aliquot every 0.5 seconds, or at least 1 sample aliquot every 0.1 seconds). This shuttle valve is further described in conjunction with a chromatography system in copending U.S. provisional patent application No. 61/005,590, the entire subject matter of which is incorporated herein by reference.

II. Apparatus for Moving Aliquot Samples of Fluid

The present invention is also directed to an apparatus capable of moving an aliquot sample of fluid. In one exemplary embodiment, the apparatus for moving an aliquot sample of fluid comprises hardware operatively adapted to remove a very small sample volume, or aliquot, of fluid from a much larger volume of fluid, such as the flow of a stream through a channel. The disclosed apparatus of the present invention may also be utilized to remove a very small sample volume, or aliquot, of fluid from a much larger volume of fluid, such as the flow of a stream through a channel, and transfer the sample to another volume of fluid or container.

In one exemplary embodiment, an apparatus capable of moving an aliquot sample of fluid comprises a first fluid, a second fluid, and a shuttle valve capable of removing an aliquot from the first fluid to the second fluid while maintaining a continuous flow path through the shuttle valve of the second fluid. In one embodiment, the apparatus is capable of removing the aliquot from the first fluid while maintaining a continuous flow path through the shuttle valve of the first fluid. In another embodiment, the apparatus is capable of removing the aliquot from the first fluid while maintaining continuous flow paths of both the first fluid and the second fluid.

In another embodiment according to the present invention, an apparatus capable of moving an aliquot sample of fluid comprises a first fluid channel, a second fluid channel, and a shuttle valve capable of removing an aliquot of fluid from the first channel to the second channel without substantially affecting the flow properties of fluid in the first channel through the valve. At least a portion of the first channel through the valve may be substantially straight. In this embodiment, the pressure of fluid in the first channel through the shuttle valve does not substantially increase. In another exemplary embodiment, at least a portion of the first channel may be substantially parallel to the aliquot dimple, which provides laminar flow of fluid in the first channel through the valve. In a further embodiment, at least a portion of the second channel through the valve may be substantially straight. In this embodiment, the pressure of fluid in the second channel through the shuttle valve does not substantially increase. In another exemplary embodiment, the second channel may be substantially parallel to the aliquot dimple, which provides laminar flow of fluid in the second channel through the valve.

In a further exemplary embodiment according to the present invention, an apparatus capable of moving an aliquot sample of fluid comprises a static body having at least two channels therethrough such that a portion of each channel intersects with a first surface of the static body, a dynamic body having an aliquot dimple that intersects with a first surface of the dynamic body, the first surface of the static body and the first surface of the dynamic body being contiguous with each other, and the channels and the aliquot dimple located such that the aliquot dimple may be in fluid communication with one channel in a first position and in fluid communication with another channel in a second position, wherein at least a portion of the first channel is substantially parallel to the first surface of the static body. In an alternative exemplary embodiment, at least a portion of the first channel through the valve may be substantially straight. In an exemplary embodiment, the pressure of fluid in the first channel through the shuttle valve does not substantially increase. In another exemplary embodiment, at least a portion of the first channel may be substantially parallel to the aliquot dimple. In an exemplary embodiment, the flow of fluid in the first channel through the valve is laminar. In a further embodiment, at least a portion of the second channel through the valve may be substantially straight. In a further embodiment, the pressure of fluid in the second channel through the shuttle valve does not substantially increase. In another exemplary embodiment, the second channel may be substantially parallel to the aliquot dimple. In an embodiment, the flow of fluid in the second channel through the valve may be laminar.

In a further exemplary embodiment according to the present invention, an apparatus capable of moving an aliquot sample of fluid comprises a static body having at least two channels therethrough such that a portion of each channel intersects with a first surface of the static body, a dynamic body having an aliquot dimple that intersects with a first surface of the dynamic body, the first surface of the static body and the first surface of the dynamic body being contiguous with each other, and the channels and the aliquot dimple located such that the aliquot dimple may be in fluid communication with one channel in a first position and in fluid communication with another channel in a second position, wherein at least a portion of the second channel is substantially parallel to the first surface of the static body.

In a further exemplary embodiment according to the present invention, an apparatus capable of moving an aliquot sample of fluid comprises a static body having at least two channels therethrough such that a portion of each channel intersects with a first surface of the static body, a dynamic body having an aliquot dimple that intersects with a first surface of the dynamic body, the first surface of the static body and the first surface of the dynamic body being contiguous with each other, and the channels and the aliquot dimple located such that the aliquot dimple may be in fluid communication with one channel in a first position and in fluid communication with another channel in a second position, wherein the shuttle valve longevity is at least about 1 million cycles, 2 million, 3 million, 4 million, 5 million, 6 million, 7 million, 8 million, 9 million, 10 million or more cycles before servicing is required.

The above-described FIGS. 1-2 depict elements of an exemplary embodiment of the apparatus according to the present invention. The configuration of the channels in the shuttle valve provides continuous flow through the valve, reduces substantial pressure increase in the streams flowing through the valve, and/or provides laminar flow through the valve.

Figure 3A:
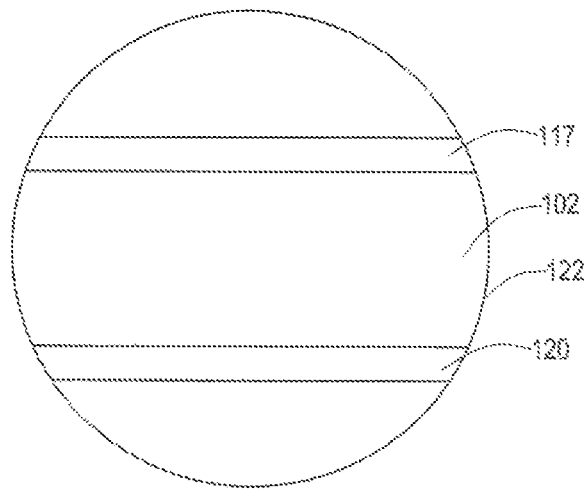
FIGS. 3A-3C depict exemplary static bodies of the shuttle valve suitable for use in the present invention.
Figure 3B:
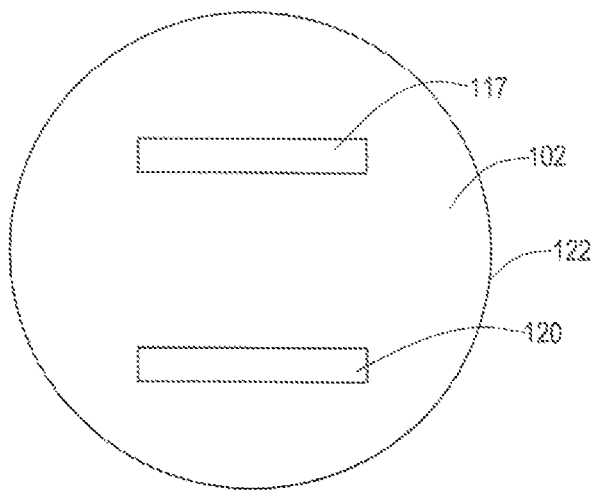
Figure 3C:
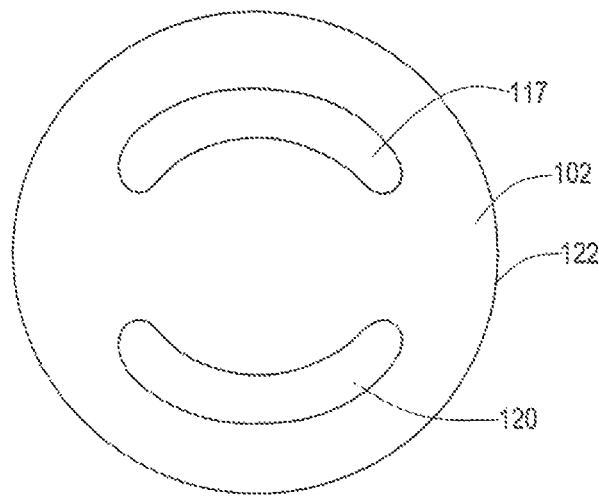

FIGS. 3A-3C depict exemplary channel configurations of the valve according to the present invention. At least a portion of the channels in the valve are substantially parallel to a first surface of the static body. For example, FIG. 3A illustrates a cross-sectional view of a shuttle valve 100 according to one exemplary embodiment of the present invention. The static body 122 includes at least two channels 117 and 120 that are parallel to a first surface 102, which are contiguous with the entire width of static body first surface 102. In an alternative exemplary embodiment, the channels 117 and 120 are parallel and contiguous with at least a portion of the first surface 102 of the static body 122 (see FIG. 3B). In a further exemplary embodiment, the channels 117 and 120 are parallel to the surface and extend in a circumferential direction (see FIG. 3C). The portion of the channels 117 and 120 that are contiguous with the first surface 102 of the static body 122 may vary in size and shape, but is typically larger than the size of the dimple 116 in the dynamic body 119. For example, the portions of the channels 117 and 120 that are contiguous with the first surface 102 of the static body 122 may be rectangular, circular, elliptical, and may be in a variety of locations on the face of the static body, but typically are located such that they will intersect with the dimple 116 when rotated from one channel 117 to the other 120.

Figure 4:
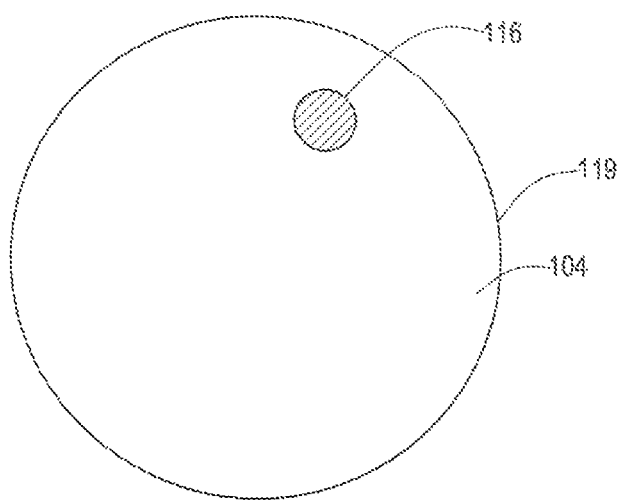
FIG. 4 depicts an exemplary dynamic body of the shuttle valve suitable for use in the present invention.

In another exemplary embodiment, the dimple 116 of the dynamic body 119 may be configured such that may be easily rotated from channel 117 to channel 120. The dimple 116 may be of any shape, e.g., rectangular, circular, elliptical, square, etc., that allows for rapid fluid or mass transfer but is depicted as a concave semi sphere, and it may be any size (see FIG. 4). In an exemplary embodiment, the dimple 116 may be extremely small in size (e.g., less than 2000 nL, preferably less than about 500 nL, more preferably less than about 100 nL, and even more preferably less than about 1 nL, but may include any size from 1 nL to 2000 nL, which allows for rapid sampling. In addition, small dimple 116 size allows for a very short dimple rotation path 121, which significantly reduces wear on the surfaces of the dynamic body 119 and the static body 122 and results in a shuttle valve 100 having extended service life before maintenance is required (e.g., more than 10 million cycles are possible before service). The dimple 116 is located on a first surface 104 of the dynamic body 119 such that it readily intersects with the channels 117 and 120.

Figure 5:
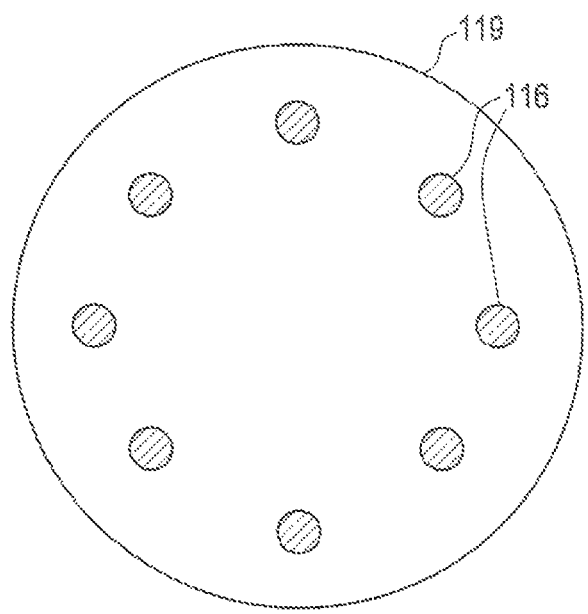
FIG. 5 depicts an exemplary dynamic body of the shuttle valve suitable for use in the present invention.

In alternative embodiments, the shuttle valve of the present invention may comprise more than two channels and/or more than one dimple, which may enable multiple transfers of aliquot samples at the same time or in rapid succession and/or multiple samples being transferred to and from multiple channels at the same time or sequentially. For example, the dynamic body 119 may include multiple dimples 116 along the same circumference such that the dynamic body only 119 rotates in one direction (FIG. 5).

Figure 6A:
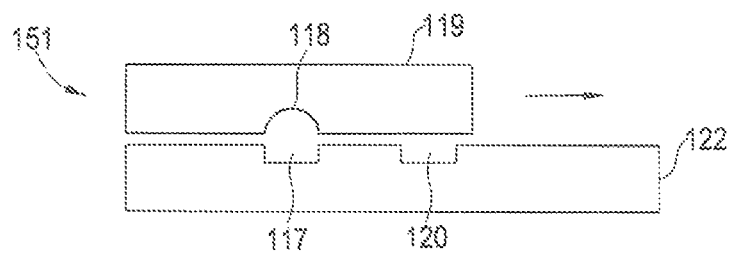
FIG. 6A-6B depicts a cross-sectional view of the operation of an exemplary shuttle valve suitable for use in the present invention.
Figure 6B:
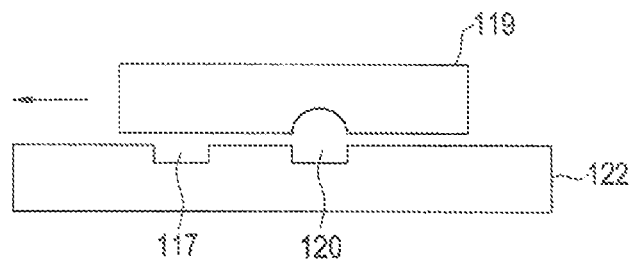

In other embodiments, the shuttle valve of the present invention may be in configurations other than those that rotate around an axis. For example, the shuttle valve may be designed such that linear motion is utilized to move the aliquot sample of fluid. FIG. 6A-B depicts a cross-sectional view of a linear motion shuttle valve 151 where the dynamic body 119 moves in a linear motion over static body 122 such that in one position (shown in FIG. 6A), dimple 118 is aligned with channel 117 and in another position (shown in 6B), dimple 118 is aligned with channel 120. In this manner, sample aliquot is transferred from channel 117 to channel 120.

In even further exemplary embodiments, the shuttle valve 100 is constructed such that the dynamic body 119 and static body 122 produce the least amount of wear on these parts. For example, because the dimple 116 and channels 117 and 120 are designed to minimize the number of ports, grooves or channels, and the surface area with which these openings occupy, this allows increased longevity of the shuttle valve 100 (e.g., at least about 1 million cycles, preferably at least about 2 million cycles, more preferably at least about 5 million cycles, and even more preferably at least about 10 million cycles). Additionally, this design allows for the use of increased operational pressures, such as pressures at least about 10 psi, preferably at least about 100 psi, more preferably at least about 1000 psi, and even more preferably at least about 10,000 psi (e.g., above 20,000 psi).

In an additional exemplary embodiment, the shuttle valve 100 is constructed of materials that increase the longevity of the valve. The static body 122 and dynamic body 119 are constructed of materials that are easily machined but provide suitable sealing, low torque, and resistance to wear between the static body 122 and dynamic body 119. For example, such materials include organic materials including polymeric materials such as polyethylene (e.g., high molecular weight polyethylenes), polyethers (e.g., polyetheretherketones), fluoropolymers (e.g., polytetrafluoroethylene), polypropylenes, polyamides, polyimides, etc., and blends thereof; and inorganic materials such as ceramics, metals, etc. The materials may include mixtures or composites of these materials, or may be coated with such materials. In one exemplary embodiment, the dynamic body 119 is constructed of ultra-high molecular weight polyethylene and the static body 122 is constructed of natural polyetheretherketone.

IV. Applications/Uses

The above-described methods and apparatus may be used to move an aliquot sample of fluid from one fluid to another. The above-described methods and apparatus find applicability in any industry that utilizes fluidics including, but not limited to, the petroleum industry, the pharmaceutical industry, analytical labs, etc.

Figure 7:
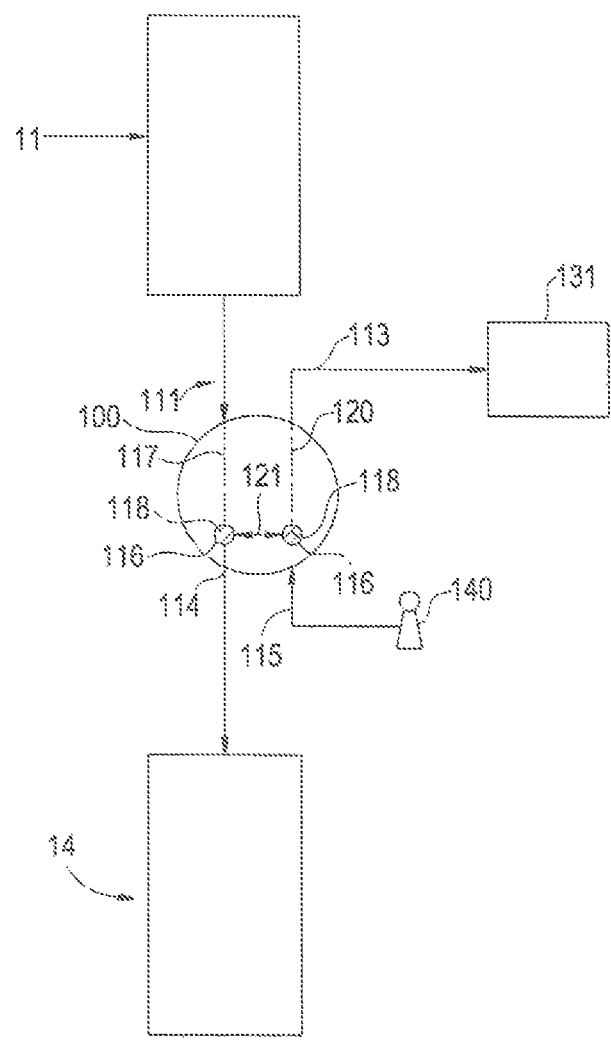
FIG. 7 depicts an exemplary shuttle valve as part of a sample analyzer suitable for use in a chromatography system.

FIG. 7 demonstrates how a shuttle valve operates within a given liquid chromatography system. As shown in FIG. 7, shuttle valve 100 comprises chromatography column inlet 111, which provides fluid flow from a chromatography column (e.g., column 11) to shuttle valve 100; an incoming sample aliquot volume 118 in dimple 116; fraction collector outlet 114, which provides fluid flow from shuttle valve 100 to a fraction collection (e.g., fraction collection 14); gas or liquid inlet 115, which provides gas (e.g., air, nitrogen, etc.) or liquid (e.g., an alcohol) flow using pump 140 through a portion of shuttle valve 100; outgoing sample aliquot volume 118; and detector outlet 113, which provides fluid flow from shuttle valve 100 to a detector (e.g., detector 131, such as a ELSD).

As fluid flows through shuttle valve 100 from chromatography cartridge to inlet 111 to fraction collector outlet 114 via channel 117, dimple 116 is filled with a specific volume of incoming sample aliquot volume 118 (shown as the shaded area in FIG. 7). At a desired time, shuttle valve 100 transfers incoming sample aliquot volume 118 in dimple 116 via dimple rotation path 121 to channel 120 as shown in FIG. 7. Once sample aliquot 118 is transferred to channel 120, gas or liquid flowing from inlet 115 through channel 120 transports sample aliquot 118 to detector 131 (e.g., an ELSD) via detector outlet 113.

Figure 8:
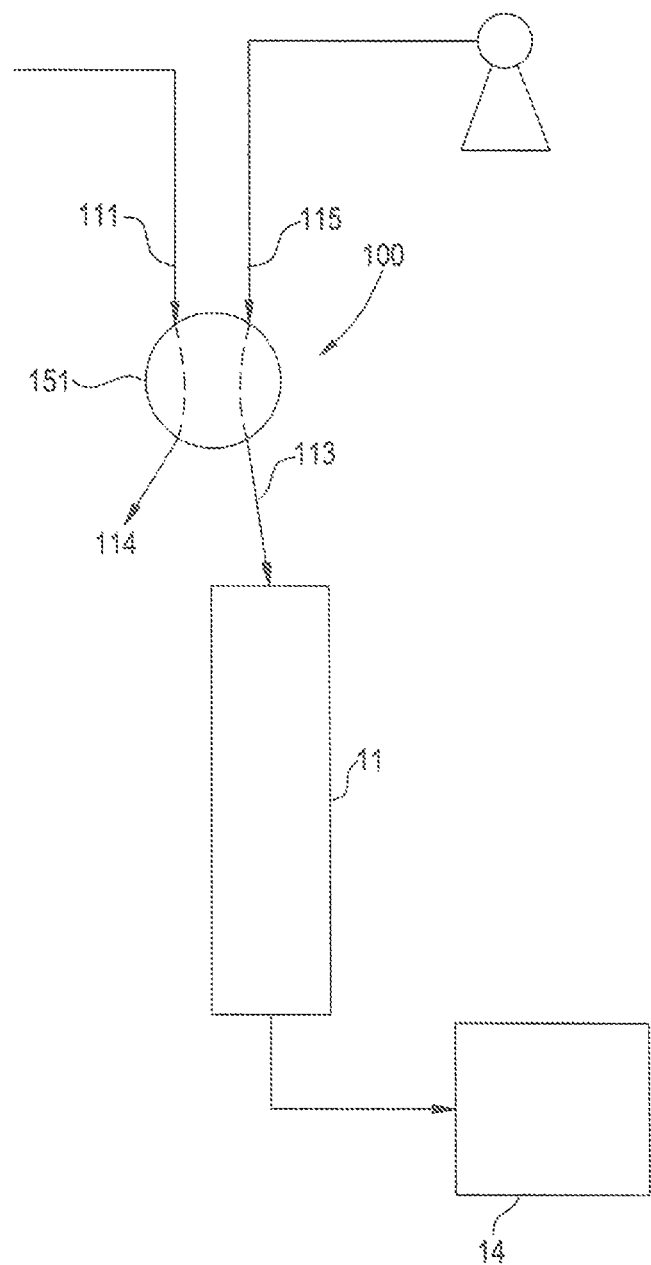
FIG. 8 depicts an exemplary shuttle valve as a sample injection valve suitable for use in a chromatography system.

In another exemplary embodiment, the shuttle valve may be utilized to transfer a single aliquot from a first fluid to a second fluid. For example, the first fluid may be introduced into the sample dimple and one single motion to place the sample aliquot into the second fluid could then be completed. In this configuration, the shuttle valve of the present invention may be utilized to inject samples for separation into chromatography systems or columns. This sample introduction is allowed to proceed through the column or system completely before another is injected. This injection mode embodiment would typically be used in more traditional HPLC applications where a single sample aliquot (one dimple volume) is fully analyzed before another sample volume is injected into the system. Since the design of the shuttle valve of the present invention allows for very small aliquot samples of fluid, this valve may also be utilized in micro and nano chromatography systems. FIG. 8 illustrates an exemplary embodiment of such a design where shuttle valve 151 is utilized to inject an aliquot from sample fluid 111 to fluid 113 and then to chromatography column 11.

In an alternative exemplary embodiment, the shuttle valve of the present invention may be utilized as a dosing device. For example, such a valve may be used in many manufacturing processes including industries such as pharmaceuticals, food flavoring, chemical dosing, recreational water (pool and spa) chemical introduction, and agricultural distribution of fertilizers. In one exemplary embodiment, dosing apparatus may include two flow paths, each flowing at their own flow rates. Chemical A is introduced into the main flow path at a particular rate. With another valve of the present invention, a second chemical B could be introduced into the second flow path at a discrete rate. With multiple valves, complex chemical additions could be added to flowing streams and the streams dispensed into multiple containers of product. Mixing would be accomplished simultaneously as the chemical is introduced into the stream(s) since the flow of the stream naturally mixes the added chemical. On a large dosing volume scale, many consumer products are produced with a main carrier component such as water. As opposed to dispensing with pumps requiring cleaning and maintenance, the valve of the present invention provides a simple alternative for certain applications. On a smaller scale, a dosing apparatus may include a shuttle valve of the present invention to produce routine mixtures of chemicals at any component concentration. Alternatively, if gravity is used to introduce chemical doses, the shuttle valve of the present invention may be utilized whereby disposable containers of the dosing chemical may be temporarily attached to the valve and replaced at specified intervals. In this embodiment, pumping equipment may not be required, thereby saving on the cost of additional hardware. This may be advantageous in various markets such as the agricultural business and also for home use as chemicals could be distributed in certain applications using low power consumption (e.g., solar power).

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

In this example, the flash REVELERIS™ system (available from Grace Davison Discovery Sciences) was utilized. 4 mL of a mixture containing dioctyl phthalate and butyl paraben was injected into a 4 g GRACERESOLVE™ C18 flash cartridge (available from Grace Davison Discovery Sciences), which was mounted in the flash system. A 80/20 methanol/water mobile phase was pumped through the system using an ALLTECH™ model 300 LC pump. The column effluent was directed to a shuttle valve as described herein that diverted 300 uL/min of the column effluent to an ALLTECH™ 3300 ELSE). The balance of the effluent flowed through an Ocean Optics UV detector to a Gilson fraction collector.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A method of moving an aliquot sample of fluid from a first fluid to a second fluid, said method comprising the steps of: (a) providing the first fluid, (b) providing the second fluid, and (c) using a shuttle valve to remove the aliquot sample of fluid from the first fluid and input the aliquot sample of fluid into the second fluid while maintaining a continuous flow path of the second fluid through the shuttle valve, wherein a continuous flow path of the first fluid and a continuous flow path of the second fluid is maintained through the shuttle valve as the aliquot sample of fluid is removed from the first fluid and inputted into the second fluid.

2. A method of moving an aliquot sample of fluid, said method comprising the steps of:
 (a) providing a first fluid, and
 (b) using a shuttle valve to remove the aliquot sample of fluid from the first fluid and input the aliquot sample of fluid into a second fluid flowing through the shuttle valve while maintaining (i) continuous flow of the first fluid through the shuttle valve and (ii) continuous flow of the second fluid through the shuttle valve.

3. The method according to claim 2, wherein fluid flow of the first fluid through the shuttle valve is substantially laminar.

4. The method according to claim 2, wherein pressure of the first fluid through the shuttle valve remains substantially constant.

5. A method of moving an aliquot sample of fluid, said method comprising the steps of:
 (a) providing a static body having at least two channels therethrough such that a portion of each of the at least two channels intersects with a first surface of the static body,
 (b) providing a dynamic body having an aliquot dimple that intersects with a first surface of the dynamic body, the first surface of the static body and the first surface of the dynamic body being contiguous with each other and the at least two channels and the aliquot dimple located such that the aliquot dimple is in fluid communication with one channel of the at least two channels in a first position and in fluid communication with another channel of the at least two channels in a second position, (c) continuously flowing, a first fluid through one of the in least two channels, continuously flowing a second fluid through another of the at least two channels, aligning the aliquot dimple in the first position, allowing the aliquot sample, from the first fluid, to flow into the aliquot dimple, and (d) moving the aliquot dimple to the second position, whereby the aliquot sample is transferred to the second fluid while the first fluid and the second fluid continuously flow through the at least two channels, wherein at least a portion of at least one channel of the at least two channels is substantially parallel to the first surface of the static body.

6. An apparatus capable of moving an aliquot sample of fluid, said apparatus comprising: (a) a first fluid path, (b) a second fluid path, and (c) a shuttle valve capable of removing the aliquot sample of fluid from the first fluid path and inputting the aliquot sample of fluid into the second fluid path while maintaining continuous flow of a fluid through the second fluid of the shuttle valve, wherein the shuttle valve is capable of removing the aliquot sample of fluid from the first fluid path while maintaining continuous flow of a first fluid within the first fluid path and continuous flow of a second fluid within the second fluid path of the shuttle valve.

7. An apparatus capable of moving an aliquot sample of fluid, said apparatus comprising:
(a) a first fluid path,
(b) a second fluid path, and
(c) a shuttle valve capable of removing the aliquot sample of fluid from the first fluid path and inputting the aliquot sample of fluid into the second fluid path while maintaining (i) continuous fluid flow in the first fluid path through the shuttle valve and (ii) continuous fluid flow in the second fluid path through the shuttle valve.

8. The apparatus according to claim 7, wherein the continuous fluid flow in the first fluid path through the shuttle valve is substantially laminar.

9. The apparatus according to claim 7, wherein pressure in the first fluid path through the shuttle valve remains substantially constant.

10. An apparatus capable of moving an aliquot sample of fluid, said apparatus comprising:
(a) a static body having at least two paths therethrough such that a portion of each path of said at least two paths intersects with a first surface of the static body, and
(b) a dynamic body having an aliquot dimple that intersects with a first surface of the dynamic body, the first surface of the static body and the first surface of the dynamic body being contiguous with each other and the at least two paths and the aliquot dimple being located such that the aliquot dimple is in fluid communication with a first path of said at least two paths in a first position and in fluid communication with a second path of said at least two paths in a second position, said static body and said dynamic body being movable relative to one another so as to move said aliquot dimple from said first position to said second position while maintaining continuous fluid flow through said first path and said second path, wherein at least a portion of the first path is substantially parallel to the aliquot dimple.

11. The apparatus according to claim 10, wherein at least a portion of the first path is parallel to the first surface of the static body.

12. The apparatus according to claim 10, wherein at least to portion of the second path is parallel to the first surface of the static body.

13. The apparatus according, to claim 10, wherein the apparatus further comprises a dosing device.

14. The apparatus according to claim 10, wherein the apparatus further comprises a sample removal device for sample analysis.

15. The apparatus according to claim 10, wherein the apparatus further comprises a sample injection device for chromatography systems.

16. The apparatus according to claim 10, wherein the apparatus is capable of performing at least about 5 million aliquot sample transfers from the first path to the second path before servicing of the apparatus is required.

17. The apparatus according to claim 10, wherein the dynamic body is constructed of ultrahigh molecular weight polyethylene and the static body is constructed of natural polyetheretherketone.

* * * * *